US009414959B2

(12) United States Patent
Belson

(10) Patent No.: US 9,414,959 B2
(45) Date of Patent: Aug. 16, 2016

(54) GASTRIC, CUTANEOUS, OR PERITONEAL DELIVERY OF FROZEN MIST TO INDUCE THERAPEUTIC HYPERTHERMIA

(75) Inventor: Amir Belson, Los Gatos, CA (US)

(73) Assignee: Qool Therapeutics, Inc., Menlo Park, CA (US)

( * ) Notice: Subject to any disclaimer, the term of this patent is extended or adjusted under 35 U.S.C. 154(b) by 210 days.

(21) Appl. No.: 13/603,955

(22) Filed: Sep. 5, 2012

(65) Prior Publication Data

US 2013/0085554 A1      Apr. 4, 2013

Related U.S. Application Data

(60) Provisional application No. 61/531,052, filed on Sep. 5, 2011.

(51) Int. Cl.
*A61F 7/12*      (2006.01)
*A61F 7/00*      (2006.01)
*A61F 7/02*      (2006.01)

(52) U.S. Cl.
CPC .............. *A61F 7/0085* (2013.01); *A61F 7/02* (2013.01); *A61F 7/12* (2013.01); *A61F 2007/0063* (2013.01); *A61F 2007/0069* (2013.01); *A61F 2007/0234* (2013.01); *A61F 2007/126* (2013.01)

(58) Field of Classification Search
CPC .................. A61B 18/0218; A61B 2018/0293; A61F 2007/0018; A61F 2007/0063; A61F 2007/0064; A61F 2007/0069; A61F 2007/0234; A61F 2007/126; A61F 7/0085; A61F 7/12

USPC .............. 606/20–22; 607/104, 105, 107, 112, 607/113; 604/113; 62/259.3

See application file for complete search history.

(56) References Cited

U.S. PATENT DOCUMENTS

| 5,997,530 | A | 12/1999 | Nelson et al. |
|---|---|---|---|
| 6,141,985 | A | 11/2000 | Cluzeau et al. |
| 6,303,156 | B1 | 10/2001 | Ferrigno |
| 6,306,119 | B1 | 10/2001 | Weber et al. |
| 6,547,811 | B1 | 4/2003 | Becker et al. |
| 6,764,493 | B1 * | 7/2004 | Weber et al. .................. 606/131 |
| 8,100,123 | B2 | 1/2012 | Belson |
| 8,465,535 | B2 | 6/2013 | Harris et al. |

(Continued)

FOREIGN PATENT DOCUMENTS

| JP | H 11-342149 A | 12/1999 |
|---|---|---|
| WO | WO 99/66938 A1 | 12/1999 |

(Continued)

OTHER PUBLICATIONS

International search report and written opinion dated Nov. 15, 2012 for PCT/US2012/053809.

(Continued)

*Primary Examiner* — Michael Peffley
*Assistant Examiner* — Thomas Giuliani
(74) *Attorney, Agent, or Firm* — Wilson Sonsini Goodrich & Rosati

(57) ABSTRACT

Peritoneal heat exchange provides the benefit of extremely rapid cooling of the patient's target organs such as the heart and brain as well as facilitating global patient body temperature reduction to therapeutically effective temperatures. The heat exchange medium of the present invention is a chilled gaseous fluid suspension of frozen ice particles.

9 Claims, 6 Drawing Sheets

(56) References Cited

U.S. PATENT DOCUMENTS

| | | | |
|---|---|---|---|
| 2003/0066304 A1* | 4/2003 | Becker et al. | 62/330 |
| 2003/0131844 A1 | 7/2003 | Kumar et al. | |
| 2003/0136402 A1 | 7/2003 | Jiang et al. | |
| 2004/0092920 A1* | 5/2004 | Rozenshpeer | 606/22 |
| 2005/0101911 A1 | 5/2005 | Chester et al. | |
| 2005/0279108 A1* | 12/2005 | Akselband et al. | 62/121 |
| 2006/0069418 A1* | 3/2006 | Schock et al. | 607/104 |
| 2008/0039911 A1 | 2/2008 | Koninckx et al. | |
| 2008/0209932 A1* | 9/2008 | Clarke et al. | 62/259.3 |
| 2009/0107491 A1 | 4/2009 | Belson | |
| 2010/0185174 A1* | 7/2010 | Boyden et al. | 604/503 |
| 2012/0167878 A1 | 7/2012 | Belson et al. | |

FOREIGN PATENT DOCUMENTS

| | | |
|---|---|---|
| WO | WO 01/08593 A2 | 2/2001 |
| WO | WO 01/08593 A3 | 3/2002 |
| WO | WO 03/047503 A2 | 6/2003 |
| WO | WO 03/059425 A1 | 7/2003 |
| WO | WO 03/047503 A3 | 12/2003 |
| WO | WO 2009/009540 A1 | 1/2009 |

OTHER PUBLICATIONS

European search report and opinion dated Apr. 15, 2015 for EP Application No. 12829249.7.

* cited by examiner

GASTRIC, CUTANEOUS, OR PERITONEAL DELIVERY OF FROZEN MIST TO INDUCE THERAPEUTIC HYPERTHERMIA

CROSS-REFERENCE

This application claims the benefit of U.S. Provisional Application No. 61/531,052, filed Sep. 5, 2011, which is incorporated herein by reference in its entirety.

BACKGROUND OF THE INVENTION

1. Field of the Invention

The present invention relates generally to apparatus and methods for selective modification and control of a patient's body temperature. More particularly, it relates to relatively non-invasive and field operable systems and methods of lowering a patient's body temperature by heat exchange within the patient's peritoneum. Peritoneal heat exchange provides the benefit of extremely rapid cooling of the patient's target organs such as the heart and brain as well as facilitating global patient body temperature reduction to therapeutically effective temperatures. The heat exchange medium of the present invention is a chilled gaseous fluid suspension of frozen ice particles.

2. Background of the Invention

Man is considered to be a tropical animal. Normal functioning of the human animal requires a body temperature of approximately 37 degrees Celsius (98.6 degrees Fahrenheit). The body can self-compensate for small upward or downward variations in temperature through the activation of a built-in thermoregulatory system, controlled by temperature sensors in the skin. The response to an upward variation in body temperature is the initiation of perspiration, which moves moisture from body tissues to the body surface. When the moisture reaches the surface it evaporates, carrying with it a quantity of heat. The explanation for a person becoming thirsty when exposed to a hot environment for a period of time is that fluids lost due to perspiration must be replaced. The response to a downward variation in body temperature is shivering, which is the body's attempt to generate heat. Shivering is an involuntary contraction and expansion of muscle tissue occurring on a large scale. This muscle action creates heat through friction.

Hypothermia is defined as a core temperature of less than 35 degrees Celsius. Hypothermia is also considered the clinical state of subnormal temperature when the body is unable to generate sufficient heat to effectively maintain functions. Many variables contribute to the development of hypothermia. Age, health, nutrition, body size, exhaustion, exposure, duration of exposure, wind, temperature, wetness, medication and intoxicants may decrease heat production, increase heat loss, or interfere with thermostability. The healthy individual's compensatory responses to heat loss via conduction, convection, radiation, evaporation and respiration may be overwhelmed by exposure. Medications may interfere with thermoregulation. Acute or chronic central nervous system processes may decrease the effectiveness of thermoregulation.

Mild Hypothermia is when the core temperature is 34-35 degrees Celsius. The patient is still alert and able to help him/herself and intense shivering begins. The patient's movements, however, become less coordinated and the coldness creates some pain and discomfort.

Moderate hypothermia is when the patient's core temperature is 31-33 degrees Celsius. Shivering slows or stops, muscles begin to stiffen and mental confusion and apathy sets in. Speech becomes slow, vague and slurred, breathing becomes slow and shallow, and drowsiness and strange behavior may occur.

Severe hypothermia is when the core temperature drops below 31 degrees Celsius. Skin is cold, may be bluish-gray in color, eyes may be dilated. The patient is very weak, displays a marked lack of coordination, slurred speech, appears exhausted, may appear to be drunk, denies there is a problem and may resist help. There is a gradual loss of consciousness. There may be little or no apparent breathing, the patient may be very rigid, unconscious, and may appear dead.

Simple methods for treating hypothermia have been known since very early times. Such methods include wrapping the patient in blankets, administering warm fluids by mouth, and immersing the patient in a warm water bath. Even these simple methods may be effective if the hypothermia is not too severe. These simple methods are limited in their effectiveness however. Wrapping the patient in blankets ultimately depends on the patient's own production of heat to rewarm his body. In even moderate cases of hypothermia, or in the case of an ill or injured patient, the patient may simply be too weak or exhausted to produce sufficient heat. Oral administration of a warm fluid requires that the patient be conscious and capable of swallowing the fluid. Since loss of consciousness occurs early in hypothermia, this method is also limited to moderate cases. Immersion of the patient in a warm water bath is often simply impractical. For example, immersion of a patient undergoing surgery would obviously be undesirable. Furthermore, the immersion technique is time consuming and may be ineffective in that it requires the transmission of warmth from the patient's skin surface into the body core before the benefit of the warmth can be realized. Other devices allow for the direct warming of a patient's blood. These methods involve removing blood from the patient, warming the blood in external warming equipment, and delivering the blood back into the patient. While such methods are much more effective than any of the simple methods previously described, they are disadvantageous for other reasons. First, the apparatus involved is quite cumbersome. Second, some danger is involved in even the temporary removal of significant quantities of blood from an already weakened patient. In fact, a further drop in body temperature is often experienced when blood is first removed for warming in the external apparatus. Finally, special catheters are used for the direct warming of a patient's blood. However, those catheters require a trained staff to insert the device to a central blood vessel of the patient and those physicians are available only in specific units and not in the ambulance or even not always in the emergency room. Those instruments are also very expensive and thus are not available for every caregiver.

Recent medical reports have described the use of controlled hypothermia as a means to reduce oxygen consumption of tissue, such as the heart muscle and the brain during decreased perfusion that occurs as a result of myocardial infarction and ischemic stroke (respectively), which leads to reduced damage and decrease of the infarcted area. Medical reports have also described the prophylactic use of controlled hypothermia during cardiac surgery or interventional cardiology procedures for reducing damage from ischemia and/or embolization in the heart and brain during and after the procedure.

The ability to prevent or greatly reduce long term damage to cardiac or brain tissue while treating patients for myocardial infarction and stroke provides a compelling need for methods and systems for purposefully inducing therapeutic hypothermia in controlled effective manner. Such systems are ideally portable and deployable by emergency medical responders in the field and must be capable of rapidly cooling vital heart and brain tissues to prevent as much damage as possible. As of yet an ideal system or method for rapidly inducing hypothermia non-invasively and outside of a critical care hospital setting does not exist. Cooling blankets offer a portable easily deployable means of chilling a patient but the body's own thermoregulatory mechanisms counteract the cooling mechanisms of such blankets through vasoconstriction. As a result cooling blankets are not able to induce hypothermia in the patient in clinically relevant time span. Ice baths are capable of reducing patient body temperature rapidly due to the large thermal gradient and large specific heat capacity of the cooling medium. However ice baths are not portable are inconsistent with necessary concurrent interventions required for treatment of MI and stroke, such as balloon angioplasty. Peritoneal catheters equipped with heat exchangers are capable of rapid cooling of the patient but the size required of such catheters makes their deployment invasive. Additionally such catheterizations require skilled technicians and must be performed in the hospital. By the time a patient has reached a hospital much critical time has been lost. Field deployable respiratory cooling systems that operate by using the body's own lungs as heat exchangers and use a gaseous fluid suspension of frozen particles as a convective cooling medium are capable of inducing hypothermia in clinically relevant time spans. However, often in medical emergencies such as stroke or MI the patient exhibits poor or depressed respiration. Additionally, respiratory cooling mechanisms have yet to match cooling rates of peritoneal cooling.

The following patents and patent applications describe apparatus and methods for affecting a patient's body temperature. These, and all other patents and patent applications referred to herein, are hereby incorporated by reference in their entirety.

3. Background Art

U.S. Pat. No. 8,100,123 and US2012/0167878 commonly assigned with the present application describe method and systems for delivering a frozen mist in a breathing gas to a patient to achieve hypothermia. The full disclosures of these patent documents are incorporated herein by reference.

WO03059425 Method for altering the body temperature of a patient using a nebulized mist—Body temperature reducing method involves administering nebulized mist at temperature below body temperature of patient until patient's temperature 2 is reduced.

US20030136402 Method for altering the body temperature of a patient using a nebulized mist—Body temperature reducing method involves administering nebulized mist at temperature below body temperature of patient until patient's temperature is reduced.

U.S. Pat. No. 6,303,156 Noninvasive method for increasing or decreasing the body temperature of a patient—Increasing or decreasing body temperature for treating e.g. hemorrhagic shock comprises administering oxygen and sulfur hexafluoride gas mixture by hyperventilation.

EP1089743 Composition containing sulfur hexafluoride and oxygen, for increasing or decreasing the body temperature of a patient—Increasing or decreasing body temperature for treating e.g. hemorrhagic shock comprises administering oxygen and sulfur hexafluoride gas mixture by hyperventilation.

WO9966938 Composition containing sulfur hexafluoride and oxygen, for increasing or decreasing the body temperature of a patient—Increasing or decreasing body temperature for treating e.g. hemorrhagic shock comprises administering oxygen and sulfur hexafluoride gas mixture by hyperventilation.

US20030066304 Method for inducing hypothermia. Hypothermia-inducing treatment method for patient in cardiac arrest involves performing continuous administering of phase-change particulate slurry to patient in cardiac arrest until state of hypothermia is induced to patient.

U.S. Pat. No. 6,547,811 Method for inducing hypothermia—Improvement of a cardiac arrest patient's outcome by pre-hospital administration of a phase-change particulate slurry internally until a state of hypothermia is induced.

WO00108593 Method for inducing hypothermia—Improvement of a cardiac arrest patient's outcome by pre-hospital administration of a phase-change particulate slurry internally until a state of hypothermia is induced.

US20030131844 Inducing hypothermia and rewarming using a helium-oxygen mixture—Composition useful for treating ischemic event by inducing hypothermia comprises a gas mixture comprising helium and oxygen having temperature significantly different than normal human body temperature.

WO03047603 Breathable gas mixtures to change body temperature—Composition useful for treating ischemic event by inducing hypothermia comprises a gas mixture comprising helium and oxygen having temperature significantly different than normal human body temperature.

SUMMARY OF THE INVENTION

The present invention provides methods and systems for the improved cooling of a patient to selectively induce hypothermia. The methods and systems rely on producing a flowing gas stream, which carries an entrained mist or suspension of frozen solid particles. The flowing gas stream is passed by or over a body surface which is not part of the patient's respiratory system, and at least some of the frozen mist particles will melt such that the resulting phase change in absorbs large amounts of the body heat, thus reducing the body temperature. The enthalpic heat absorption resulting from the phase change from the frozen particles melting (or in some cases, subliming) provides much greater heat absorption than would be possible using a cooled gas stream by itself. Cooling of body surfaces other than those in the respiratory system is also advantageous in that many such surfaces can be easily accessed and it is not necessary that the patient be breathing at the time of the treatment.

In a first aspect of the present invention, a method for cooling the patient comprises generating a mist of frozen solid particles in a flowing gas stream. The flowing gas stream is passed over a targeted body surface which is not part of the patient's respiratory system. The solid particles melt or sublime to absorb body heat to lower the patient's body temperature. The body surface will often be part of a body cavity, typically being within a patient's abdominal cavity or stomach. Alternatively, the body surface may be an external surface, such as the skin over the patient's torso.

When cooling a body cavity, the flowing gas stream is typically passed through an abdominal wall and the gas stream (which would otherwise accumulate within the body cavity) is also removed through the abdominal wall. Typically, inlet and outlet conduits are positioned through the abdominal wall, and the flowing gas stream is introduced through the inlet conduit and removed through the outlet conduit. Often, separate inlet and outlet conduits will be used and introduced through opposed locations on the abdominal wall in order to promote more complete circulation within the body cavity. In other cases, the inlet and outlet conduits may be combined in a single structure which is introduced through a single penetration in the abdominal wall.

In an alternative embodiment, the patient's skin or torso is exposed. The skin or torso will usually be covered with a jacket or similar structure which covers at least a portion of the torso and which constrains the flowing gas stream so that it effectively cools the patient's skin. The jacket may be in the form of a "bladder" or other sealed system, in which case the flowing gas stream would recirculate within a sealed exterior and the transfer would take place over a wall of the jacket. In other cases, the jacket may be opened so that the flowing gas stream is allowed to directly contact the skin for a more efficient heat transfer.

The mist of frozen particles is typically generated by cooling the flowing gas stream and injecting liquid droplets into the stream so that they freeze in situ. Cooling the gas may be effected in conventional manners, often by expansion through an expansion valve in order to cause adiabatic cooling. Optionally, the droplets or liquid which is formed into the droplets may also be cooled before they are injected into the flowing gas stream. The liquid and gas may comprise any suitable, biocompatible fluids which provide for significant enthalpic heat absorption where the frozen particles will melt or sublime at body temperature. Most commonly, the liquid will be water and the gas will be air, nitrogen, heliox, $HF_6$, carobon dioxide or another common gas. In other instances, however, the gas particles could be frozen carbon dioxide (dry ice) which would sublime when exposed to the body surface in order to absorb heat. Dry ice could optionally be provided as a solid mass, where the mass is broken down into small particles which can be injected into a flowing gas stream (therefore the gas stream need not be cooled or as cooled).

In a further aspect of the present invention, the system for cooling a patient comprises a generator which produces a mist of frozen particles in a flowing gas stream. The system further comprises a mechanism for directing the flowing gas stream to a body surface which is not part of a patient's respiratory system. Optionally, the frozen mist generator may be created without freezing a liquid in a chilled gas stream. Rather the frozen particle mist is created in a separate production apparatus such as a nebulizer or ice fog machine. An ice fog machine is typically capable of chilling a solution of air with high humidity below the freezing point of water. Small ice crystals nucleate to form a suspension of frozen particle mist of small ice particles. The frozen particle mist may then be further mixed with a chilled gaseous fluid stream an un-chilled gaseous fluid stream or used on its own.

The generator may comprise a chiller for cooling the gas, a pump for producing the flowing gas stream, and a nozzle for injecting a liquid into the cooled, flowing gas stream. The directing means comprise of a tubular member for penetrating an abdominal wall to introduce the flowing gas stream to an abdominal cavity or stomach. Alternately, first and second tubular elements will be employed for both introducing a gas stream and for removing the gas stream from the cavity. Alternatively, the directing means can comprise a jacket for placing over the patient to direct a flow over the patient's torso.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

The basis of operation for the invention described in the following embodiments is the circulation of a chilled gaseous fluid throughout the abdominal cavity wherein the chilled fluid has a suspension or mist of frozen particles. Typically a chilled gaseous fluid is produced using a chilled fluid source which may comprise a vessel storing a gas in a compressed state and/or refrigerated state. Adiabatic expansion of the gas results in a moving stream of further chilled gas. The gas typically comprises air, HELIOX (a mixture of 20% $O_2$ and 80% $He_2$), or sulfur hexafluoride ($HF_6$) but may further comprise any biocompatible gas with specific heat capacity sufficient enough for cooling operations. The chilled gaseous fluid may alternatively be produce by an suitable refrigeration system, such electrically powered refrigerators, gas or propane powered refrigerators, or any suitable gas refrigeration's system known in the art. The frozen particles typically comprise ice and are produced by the introduction of a spray of a second fluid, typically liquid water, from a fluid source into the stream of the chilled gas. The cooling gas, having been chilled to below the freezing temperature of water freezes the water droplets. Although the particles typically comprise ice it should be appreciated that any biocompatible fluid with an appropriate freezing point, heat capacity and enthalpy of fusion may be used instead of liquid water. The suspension of frozen particles (mist) acts to augment the cooling properties of the gas/ice mixture. The latent heat required to overcome the enthalpy of fusion to melt the ice particles ensures that the cooling media temperature remains close to 0° C. and the preservation of the thermal gradient across the tissue media interface. Removing heat from the patient rapidly requires maintaining a large temperature gradient between the tissues being cooled and the cooling media. Additionally, the phase change required to melt the frozen particle mist increases the total amount of energy the chilled fluid and mist mixture can remove from the patient. The total power removed from system is proportional to the rate of addition of ice particles as shown by the calculations in Table 1 shown below.

TABLE 1

| Rate of Ice Particle Addition (liter/hour) | Power to Heat Ice from −30° C. to 0° C. (W) | Power for Solid/Liquid Phase Change (W) | Power to Heat Liquid from 0° C. to 37° C. (W) | Total Power (W) |
| --- | --- | --- | --- | --- |
| 0.25 | 3.8 | 21.5 | 10.0 | 35.2 |
| 0.5 | 7.5 | 42.9 | 19.9 | 70.4 |
| 1 | 15.1 | 85.9 | 39.8 | 140.8 |
| 2.5 | 37.7 | 214.7 | 99.6 | 352.1 |
| 5 | 75.4 | 429.5 | 199.2 | 704.1 |

The calculations assume that the ice is mixed with air at atmospheric pressure; the air ice mixture is initially at −30° C. with a volumetric flow rate of 20 l/min.

Figure 1:
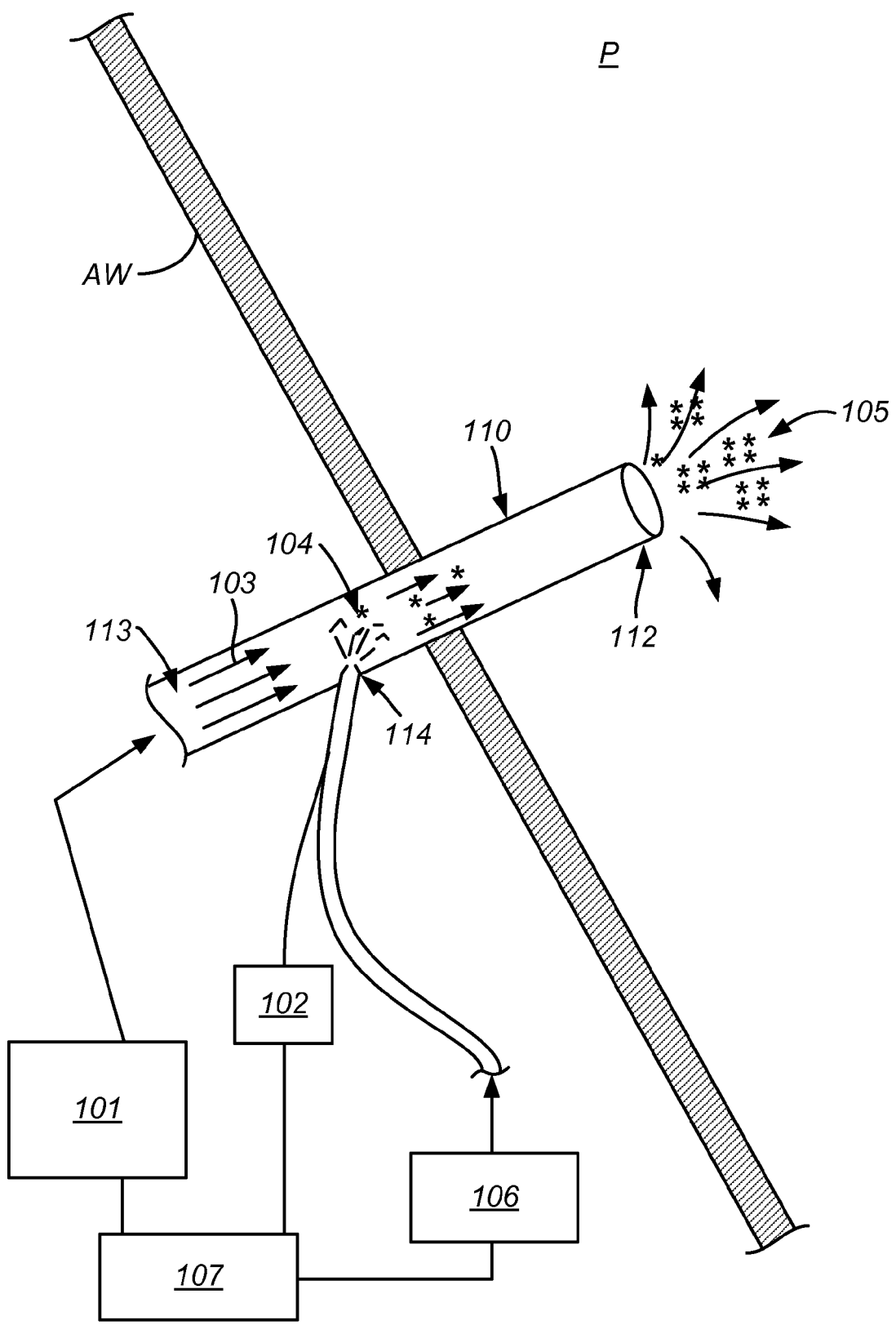
FIG. 1 shows a system that creates frozen mist through fluid spray injection into a cold gas flow.

One exemplary embodiment of the present invention is shown in FIG. 1. A main conduit 110 is shown in a patient penetrating the patient's abdominal wall AW in order to distribute a mixture of chilled gas and frozen mist into the abdominal cavity. A distal end 112 of the main conduit 110 located in a peritoneum P. A chilled fluid source 101 is connected to a main lumen 113 of the main conduit 110. A fluid port 114 allows for the introduction of a liquid from a second fluid source 102. The fluid port 114 is show proximal to the abdominal wall however it should be appreciated that the fluid port 114 may be located distal to the abdominal wall. The fluid injection port 114 may be adapted to atomize the liquid, such that a mist of small liquid droplets forms as the fluid is introduced into the chilled gas flow. The small droplets freeze as they exchange thermal energy with the chilled gaseous fluid stream 103 to form a frozen particle suspension (a mist) 104. The mixture 105 of chilled gaseous fluid 103 and frozen particle mist 104 exits the main conduit 110 into the abdominal cavity to chill tissues therein. A sensor package 106 may be used to monitor at least one of the following: patient body temperature, abdominal cavity body temperature, target organ temperature, chilled gaseous fluid flow rate, or liquid fluid introduction rate. Data measured by sensor package 106 is used may be used by a processor/controller 107 to modify the production and flow rate of the mixture 105, the flow and temperature of the gaseous fluid stream 103 in order to control the patient's temperature two within targeted therapeutic ranges. It should be understood that the fluid stream 103 and mixture 105 may not always be introduced into the patient's abdominal cavity in a continuous fashion. If the processor/controller 107 receives data from the sensor package 106 that indicates the temperature of patient's tissues are falling below the designated therapeutic range into potentially harmful ranges then the processor/controller may alter the characteristics of the gaseous fluid stream 103 or the mixture 105 or stop or retard the flow of either the gaseous fluid stream and/or the mixture 105.

Figure 2:
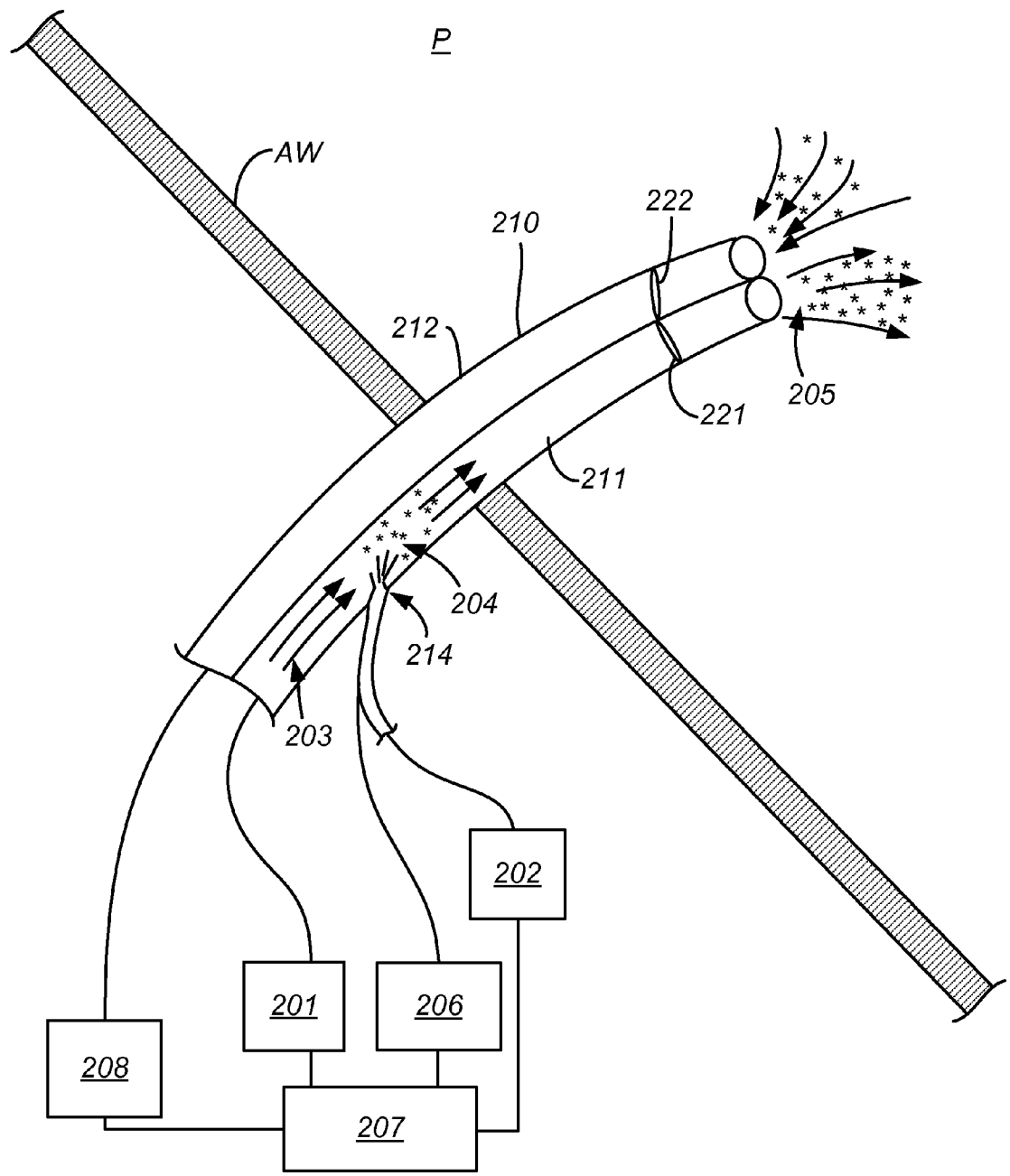
FIG. 2 shows a system a gastric tube that has two channels. One that enables inflow and the second enables outflow.

Another embodiment of the invention is shown in FIG. 2. A main conduit 210 is shown in a patient penetrating the patient's abdominal wall AW and placed into the patient's peritoneum P. The main conduit 210 comprises an inflow lumen 211 and an outflow lumen 212. The inflow lumen 211 is connected to a chilled gaseous fluid source 201. A stream of chilled gaseous fluid 203 flows through the inflow lumen 211 where it encounters a spray of liquid, typically water, introduced by the a liquid source 202 at a fluid injection port 214. The spray of liquid is frozen by the chilled gaseous fluid stream into a mist 204 of small frozen particles (typically ice). The mixture 205 of chilled gaseous fluid 203 and mist 204 proceeds from the inflow lumen 211 into the abdominal cavity of the patient to cool the patient. Thermal energy is removed from the patient as the mixture 205 is heated and the frozen particles of mist 204 melt. To facilitate further cooling the mixture 205 may be extracted out of the abdominal cavity through outflow lumen 212, which is optionally connected to a vacuum source 208. Evacuation of mixture 205 from the abdominal cavity may be accomplished via the vacuum source 208 or via passive means relying on positive pressure created in the abdominal cavity. The extraction of mixture 205 from the abdominal cavity ensures that more of mixture 205 can continue to flow through inflow lumen 211 and that the mixture 205 remains sufficiently cold relative to the patient to ensure continual rapid cooling of the patient. Inflow conduit 211 and outflow conduit 212 each have independent valves 221 and 222 respectively. This allows introduction of the mixture 205 and extraction of the mixture 205 to occur independently or simultaneously. Inflow lumen 211 and outflow lumen 212 may have different lengths, such that mixture 205 is introduced into the abdominal in a different location than mixture 205 is removed from the abdominal cavity. This may be done in an effort to prevent shunting and to better distribute the mixture 205 throughout the abdominal cavity. A sensor package 206 may be used to monitor at least one of the following: patient body temperature, abdominal cavity body temperature, target organ temperature, chilled gaseous fluid flow rate, or liquid fluid introduction rate. A processor/controller 207 is connected to the chilled gaseous fluid source 201, liquid source 202, and sensor package 206, and vacuum source 208 and is capable of controlling the functioning of any of these elements. Data measured by sensor package 206 is used may be used by a processor/controller 207 to modify the production and flow rate of the mixture 205, the amount of frozen particle mist in mixture 205, and the extraction rate of mist 205 from the abdominal cavity, and actuation of valving 221 and 222 in order to control the patient's temperature to within targeted therapeutic ranges. It should be understood that processor/controller 207 is able to independently modify the flow rate of chilled gaseous fluid 202, rate of mist 204 generation and flow rate of mixture 205, as well as extraction rate of mixture 205 from the abdominal cavity. At any point, the flow of chilled gaseous fluid 202, generation of mist 204 and flow mixture 205 into the abdominal cavity and extraction of the mixture 205 from the abdominal cavity may be independently stopped by the processor/controller 207.

Figure 3:
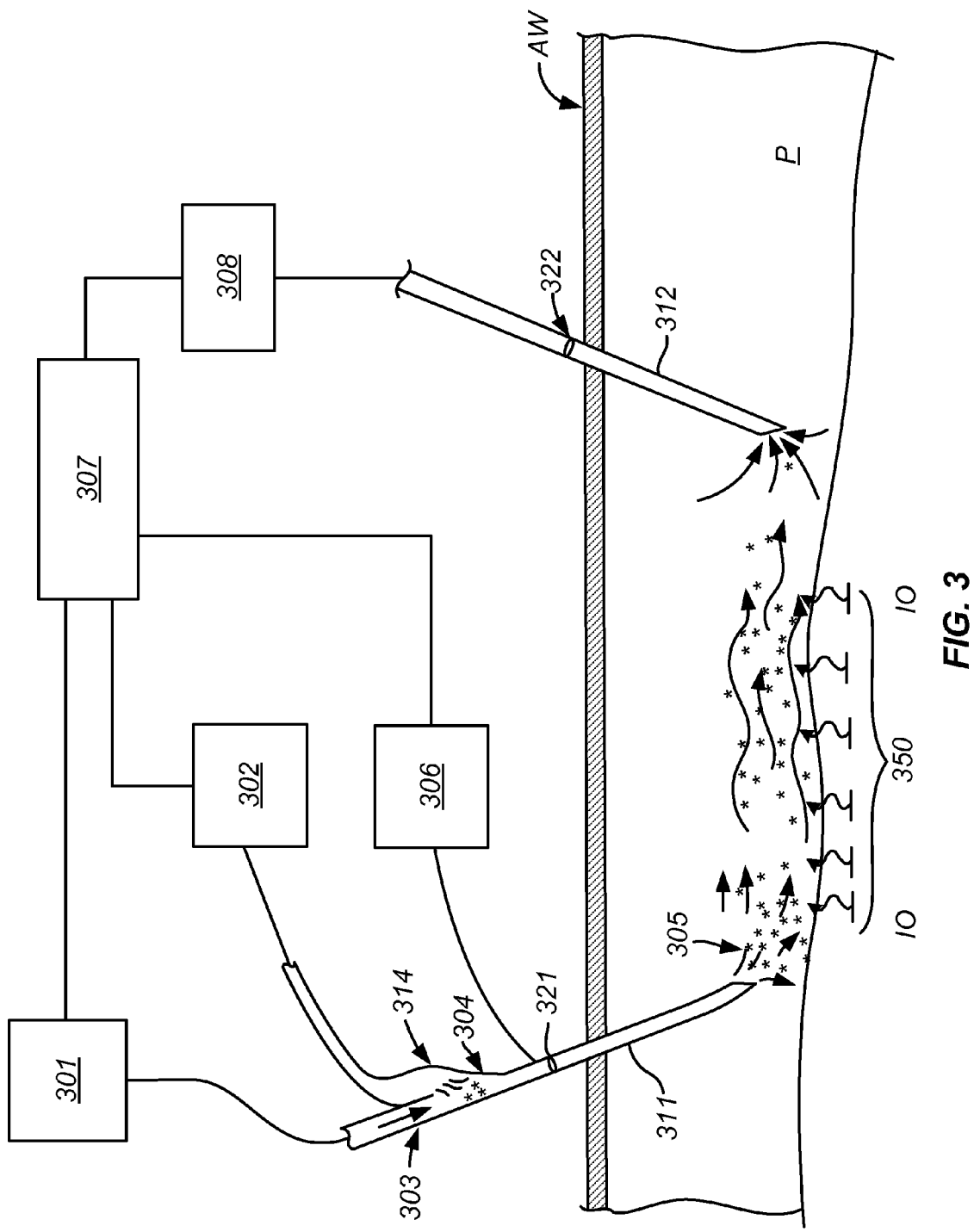
FIG. 3 shows the peritoneal mist delivery system with at least two needles.

Another embodiment of the invention is shown in FIG. 3. Two needles are shown in a patient, an inflow needle 311 and an outflow needle 312. The inflow needle 311 and outflow needle 312 are shown inserted into the patient's abdominal cavity penetrating the patient's abdominal wall AW their respective ends in the peritoneum P. Typically the inflow needle 311 and outflow needle 312 are veress needles designed to reach the peritoneum without damaging internal organs M. However, any safety needle or surgical access needle suitable for such use known to the art may be used. The inflow needle is connected to a chilled gaseous fluid source 301 which produces a stream of chilled gas 303. A Fluid injection port 314 in the inflow needle 311 connects the inflow needle 311 to a liquid fluid source 302 and produces a spray of liquid which freezes into a mist 304 of frozen particles to produce a mixture 305 of chilled gaseous fluid and frozen particle mist. The mixture 305 then exits the inflow needle into the abdominal cavity, typically in the peritoneum P. The mixture 305 is shown flowing over internal organs IO extracting heat 350 from said internal organs IO, it is understood that heat is also extracted from all tissues in the abdominal cavity that come in contact with the mixture 305. In the process of removing heat from a patient's internal organs the mixture 305 will become heated and frozen particles in the mist 304 melt. To ensure continual rapid heat extraction from the patient, the mixture 305 is extracted from the abdominal cavity through the outflow needle 312, which is optionally connected to a vacuum source 308. Vacuum source 308 may be used to aid in extraction of the mixture 305, alternatively passive extraction relying on positive partial pressure in the abdominal cavity may be used instead. Inflow needle 311 and outflow needle 312 are each equipped with independent valves 321 and 322 respectively to aid in controlling the flowrate and extraction rate of mixture 305. A sensor package 306 may be used to monitor at least one of the following: patient body temperature, abdominal cavity body temperature, target organ temperature, chilled gaseous fluid flow rate, or liquid fluid introduction rateA processor/controller 307 is connected to the chilled gaseous fluid source 301, liquid source 302, and sensor package 306, and vacuum source 308 and is capable of controlling the functioning of any of these elements. Data measured by sensor package 306 is used may be used by a processor/controller 307 to modify the production and flow rate of the mixture 305, the amount of frozen particle mist in mixture 305, and the extraction rate of mist 305 from the abdominal cavity, and actuation of valving 321 and 322 in order to control the patient's temperature to within targeted therapeutic ranges. It should be understood that processor/controller 307 is able to independently modify the flow rate of chilled gaseous fluid 302, rate of mist 304 generation and flow rate of mixture 305, as well as extraction rate of mixture 305 from the abdominal cavity. At any point, the flow of chilled gaseous fluid 302, generation of mist 304 and flow mixture 305 into the abdominal cavity and extraction of the mixture 305 from the abdominal cavity may be independently stopped or restarted by the processor/controller 307.

Figure 4:
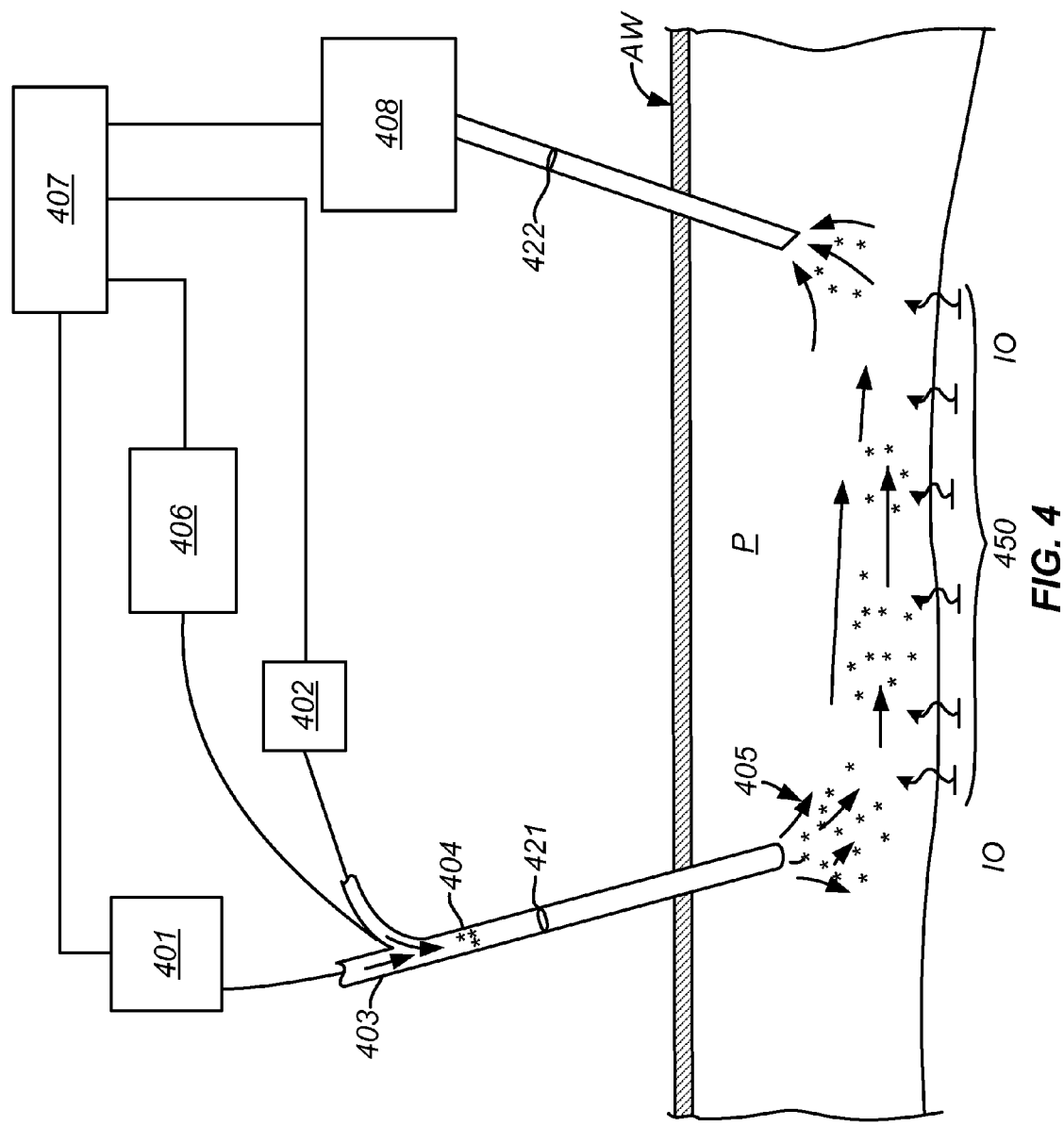
FIG. 4 shows the peritoneal mist delivery system with at least two catheters.

Another embodiment of the invention is shown in FIG. 4. Two catheters are shown in a patient's abdominal cavity an inflow catheter 411 and an outflow catheter 412. The inflow catheter 411 and outflow catheter 412 are shown inserted into the abdominal cavity penetrating the abdominal wall AW their respective ends in the peritoneum P. The inflow catheter and outflow catheter may optionally be inserted over veress needles. The inflow needle is connected to a chilled gaseous fluid source 401 which produces a stream of chilled gas 403. A Fluid injection port 414 in the inflow catheter 411 connects the inflow catheter 411 to a liquid fluid source 402 and produces a spray of liquid which freezes into a mist 404 of frozen particles to produce a mixture 405 of chilled gaseous fluid and frozen particle mist. The mixture 405 then exits the inflow catheter into the abdominal cavity, typically in the peritoneum P. The mixture 405 is shown flowing over internal organs IO extracting heat 450 from said internal organs IO, it is understood that heat is also extracted from all tissues in the abdominal cavity that come in contact with the mixture 405. In the process of removing heat from a patient's internal organs the mixture 405 will become heated and frozen particles in the mist 404 melt. To ensure continual rapid heat extraction from the patient, the mixture 405 is extracted from the abdominal cavity through the outflow catheter 412, which is optionally connected to a vacuum source 408. Vacuum source 408 may be used to aid in extraction of the mixture 405, alternatively passive extraction relying on positive partial pressure in the abdominal cavity may be used instead. Inflow catheter 411 and outflow catheter 412 are each equipped with independent valves 421 and 422 respectively to aid in controlling the flowrate and extraction rate of mixture 405. A sensor package 406 may be used to monitor at least one of the following: patient body temperature, abdominal cavity body temperature, target organ temperature, chilled gaseous fluid flow rate, or liquid fluid introduction rate. A processor/controller 407 is connected to the chilled gaseous fluid source 401, liquid source 402, and sensor package 406, and vacuum source 408 and is capable of controlling the functioning of any of these elements. Data measured by sensor package 406 is used may be used by a processor/controller 407 to modify the production and flow rate of the mixture 405, the amount of frozen particle mist in mixture 405, and the extraction rate of mist 405 from the abdominal cavity, and actuation of valves 421 and 422 in order to control the patient's temperature to within targeted therapeutic ranges. It should be understood that processor/controller 407 is able to independently modify the flow rate of chilled gaseous fluid 402, rate of mist 404 generation and flow rate of mixture 405, as well as extraction rate of mixture 305 from the abdominal cavity. At any point, the flow of chilled gaseous fluid 402, generation of mist 304 and flow mixture 405 into the abdominal cavity and extraction of the mixture 405 from the abdominal cavity may be independently stopped or restarted by the processor/controller 407.

Figure 5:
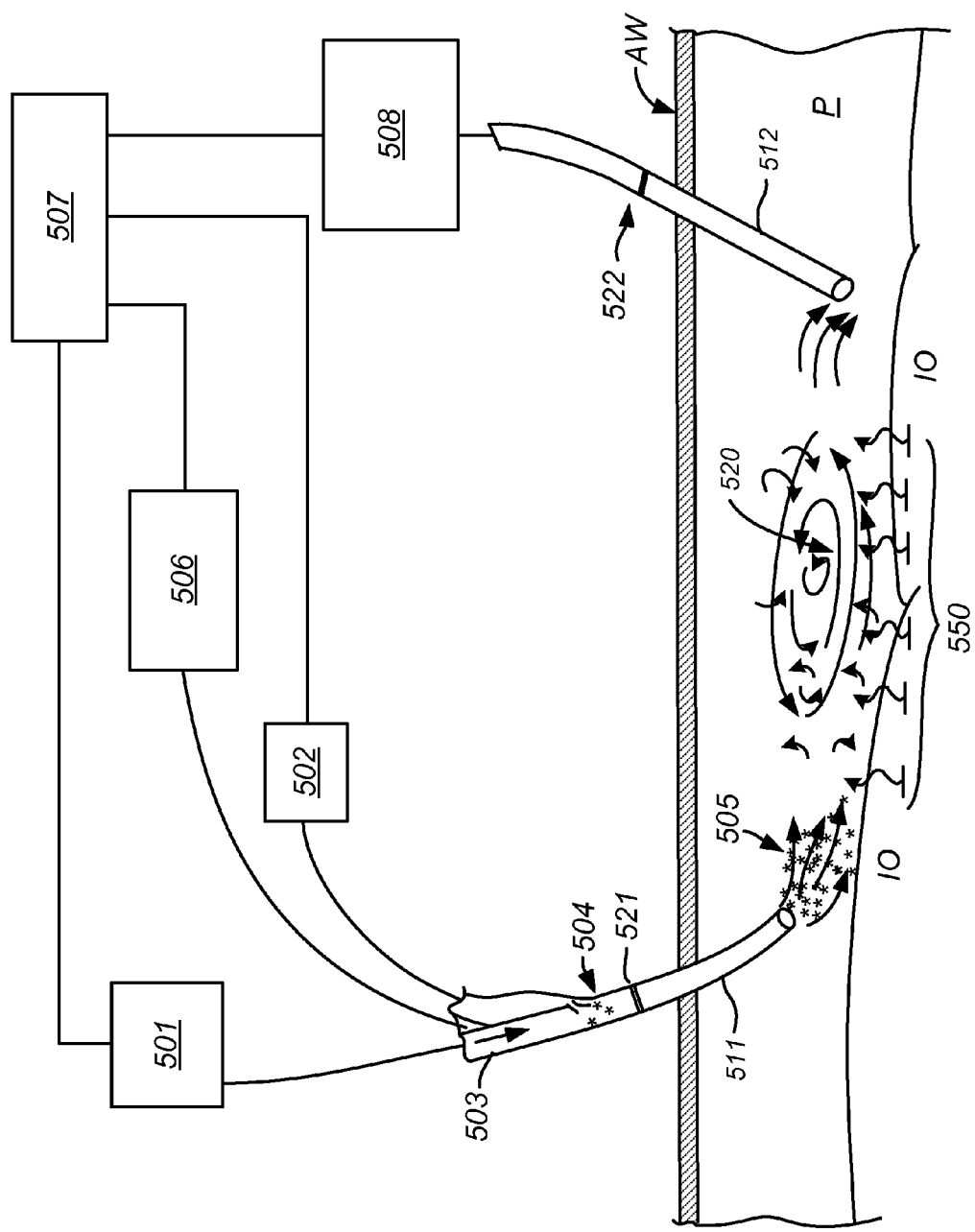
FIG. 5 shows the turbulence that may create the desired wind chill effect in the peritoneum.

Another embodiment of the invention is shown in FIG. 5. Two catheters are shown an inflow conduit 511 and an outflow conduit 512. The inflow conduit 411 and outflow conduit 412 are shown inserted into a patient's abdominal cavity penetrating the abdominal wall AW, their respective ends in the peritoneum P. The inflow conduit 511 and outflow conduit 512 may each be either a needle or catheter. The inflow conduit is connected to a chilled gaseous fluid source 501 which produces a stream of chilled gas 503. A Fluid injection port 514 in the inflow conduit 511 connects the inflow catheter 511 to a liquid fluid source 502 and produces a spray of liquid which freezes into a mist 504 of frozen particles to produce a mixture 505 of chilled gaseous fluid and frozen particle mist. The mixture 505 then exits the inflow catheter into the abdominal cavity, typically in the peritoneum P. The mixture 505 is shown flowing over internal organs IO extracting heat 550 from said internal organs IO, it is understood that heat is also extracted from all tissues in the abdominal cavity that come in contact with the mixture 505. In the process of removing heat from a patient's internal organs the mixture 505 will become heated and frozen particles in the mist 504 melt. To ensure continual rapid heat extraction from the patient, the mixture 505 is extracted from the abdominal cavity through the outflow catheter 512, which is optionally connected to a vacuum source 508. Vacuum source 508 may be used to aid in extraction of the mixture 505, alternatively passive extraction relying on positive partial pressure in the abdominal cavity may be used instead. Inflow conduit 511 and outflow conduit 512 are each equipped with independent valves 521 and 522 respectively to aid in controlling the flowrate and extraction rate of mixture 505. In this embodiment a turbulent flow 520 of mixture 505 is created in the abdominal cavity. The turbulent flow enhances the rate of heat transfer in the peritoneum by ensuring that the fluid layer of mixture 505 contacting the internal organs IO is well mixed with the rest of the mixture 505 present in the abdominal cavity. This helps to maintain a large thermal gradient between the mixture 505 and the internal organs IO ensuring maximal heat flow. The turbulent flow may be generated by means well known in the art such as modified tips for conduits 511 and 512 or by controlling the physical arrangement of conduits 511 and 512 in the abdominal cavity along with the flow rate and the pressure of mixture 505 entering and exiting the abdominal cavity through conduits 511 and 512 respectively. A sensor package 506 may be used to monitor at least one of the following: patient body temperature, abdominal cavity body temperature, target organ temperature, chilled gaseous fluid flow rate, or liquid fluid introduction rate. A processor/controller 507 is connected to the chilled gaseous fluid source 501, liquid source 502, and sensor package 506, and vacuum source 508 and is capable of controlling the functioning of any of these elements. Data measured by sensor package 506 is used may be used by a processor/controller 507 to modify the production and flow rate of the mixture 505, the amount of frozen particle mist in mixture 505, and the extraction rate of mist 505 from the abdominal cavity, and actuation of valving 521 and/522 in order to control the patient's temperature to within targeted therapeutic ranges. It should be understood that processor/controller 507 is able to independently modify the flow rate of chilled gaseous fluid 502, rate of mist 504 generation and flow rate of mixture 505, as well as extraction rate of mixture 505 from the abdominal cavity. At any point, the flow of chilled gaseous fluid 502, generation of mist 504 and flow mixture 505 into the abdominal cavity and extraction of the mixture 505 from the abdominal cavity may be independently stopped or restarted by the processor/controller 507.

Figure 6:
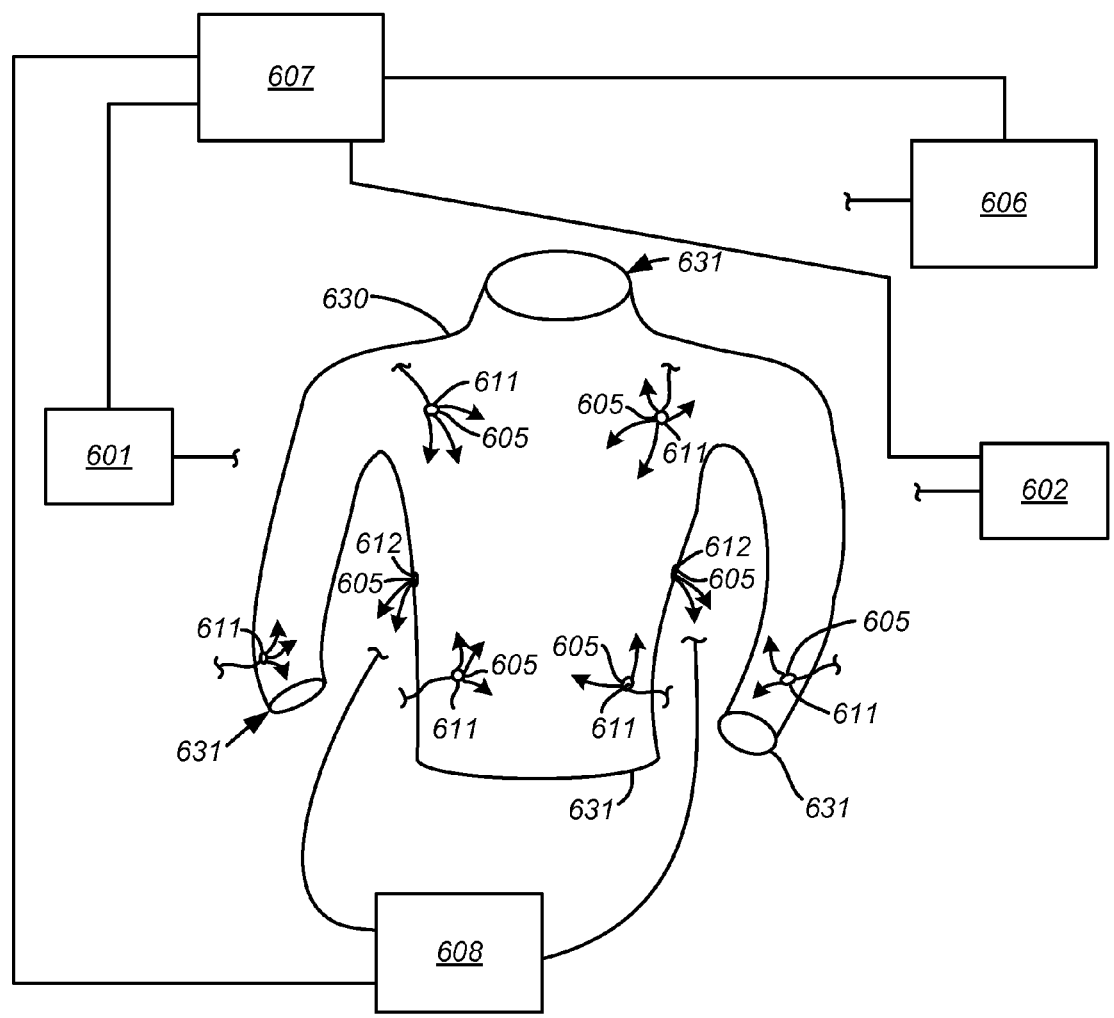
FIG. 6 illustrates a suit which covers the skin with a space for frozen mist (with or without turbulence) delivered to the skin under the suit.

In an alternative embodiment, depicted in FIG. 6, a suit 630 is shown. The suit has tightening zones 631 around the neck, belly and arms to create a substantial seal against the skin of a patient's torso. The suit has at least one inflow port 611, (multiple inflow ports shown) connected to a chilled gaseous fluid source 601 and at least one outflow port 612 (multiple outflow ports shown) connected to a vacuum source 608. A fluid liquid source 602 provides a liquid fluid spray that frozen into a frozen particle mist 604 in a stream if a chilled gaseous fluid 603 from the chilled gaseous fluid source 601 to create mixture 605 of chilled gaseous fluid 603 and frozen particle mist 604. The mixture 605 is directed through the inflow port(s) to the skin of the patients torso. The mixture 605 then conducts heat transfer across the patients torso, arms and neck removing heat from the patient through the skin to induce a state of hypothermia. The mixture 605 is removed via the at outflow port(s) 612 which are connected to a vacuum source 608. A sensor package 606 may be used to monitor at least one of the following: patient body temperature, target organ temperature, chilled gaseous fluid flow rate, or liquid fluid introduction rate. Data measured by sensor package 606 is used may be used by a processor/controller 607 to modify the production and flow rate of the mixture 605, the amount of frozen particle mist in mixture 605, and the extraction rate of mist 605 from the suit in order to control the patient's temperature to within targeted therapeutic ranges. At any point, the flow of mixture 605 into the suit and extraction of the mixture 605 from the suit may be independently stopped or restarted by the processor/controller 607.

In the embodiments shown in FIGS. 1-6 the liquid provided by the various liquid sources is typically water and the mist described in these embodiments is typically a suspension of ice particles. It should be understood that the scope of the invention is not limited to the use of liquid water. Any biocompatible frozen mist suitable for cooling purposes may be used. For instance a froze mist of dry ice may be produced by introducing finely milled dry ice particles into a chilled gas stream in order to produce the chilled fluid frozen mist mixtures described in the above embodiments.

In the embodiments shown in FIGS. 1-5, the frozen mist comprising the flowing gas stream and the frozen solid particles entrained therein may be introduced into and/or extracted from a patient's abdominal cavity (typically peritoneumor the stomach) using conventional surgical access needles or catheters, such as safety needles (e.g. veress needles), endogastric tubes, and the like.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for inducing hypothermia in a patient, said method comprising:
   selecting a patient needing hypothermic treatment;
   generating a flowing gas stream having entrained frozen solid particles; and
   passing the flowing gas stream over a body surface which is not part of the patient's respiratory system, wherein the solid particles are directly exposed to the body surface melt to absorb body heat to cause at least one of lowering and controlling the patient's body temperature, wherein passing the flowing gas stream comprises introducing the flowing gas stream through an inlet conduit in an abdominal wall into a body cavity and simultaneously removing the flowing gas stream from the body cavity through an outlet conduit in the abdominal wall and wherein the inlet conduit is separate from the outlet conduit and the conduits are introduced through opposed locations on the abdominal wall.

2. A method as in claim 1, wherein the body cavity is an abdominal cavity or a stomach.

3. A method as in claim 1, wherein generating the flowing gas stream having entrained frozen solid particles comprises cooling the flowing gas stream and injecting liquid droplets into the flowing gas stream.

4. A method as in claim 3, wherein cooling the flowing gas stream comprises expanding the flowing gas stream to cause adiabatic cooling.

5. A method as in claim 3, wherein generating the flowing gas stream having entrained frozen solid particles further comprises cooling the droplets before or as they are injected into the flowing gas stream.

6. A method as in claim 3, wherein the liquid comprises water and the gas comprises air or nitrogen.

7. A method as in claim 3, wherein the frozen particles are ice and the flowing gas stream is air or nitrogen.

8. A method as in claim 1, further comprising sensing the patient's body temperature and controlling the flow of the gas stream over the body surface to maintain the temperature within a target therapeutic range.

9. A method as in claim 1, further comprising sensing the patient's body temperature and extracting the gas stream from the body surface to maintain the temperature within a target therapeutic range.

* * * * *